United States Patent
Schweizer

(10) Patent No.: US 12,280,171 B2
(45) Date of Patent: Apr. 22, 2025

(54) STERILIZATION PACKAGING FOR STERILE PRODUCTS, HAVING A SENSOR DEVICE, AND STERILIZATION METHOD WITH ACTIVE STERILIZATION PROCESS ADAPTATION

(71) Applicant: Aesculap AG, Tuttlingen (DE)

(72) Inventor: Matthias Schweizer, Tuttlingen (DE)

(73) Assignee: Aesculap AG, Tuttlingen (DE)

( * ) Notice: Subject to any disclaimer, the term of this patent is extended or adjusted under 35 U.S.C. 154(b) by 624 days.

(21) Appl. No.: 17/283,671

(22) PCT Filed: Oct. 10, 2019

(86) PCT No.: PCT/EP2019/077511
§ 371 (c)(1),
(2) Date: Apr. 8, 2021

(87) PCT Pub. No.: WO2020/074656
PCT Pub. Date: Apr. 16, 2020

(65) Prior Publication Data
US 2022/0008590 A1    Jan. 13, 2022

(30) Foreign Application Priority Data
Oct. 11, 2018 (DE) .................... 10 2018 125 180.7

(51) Int. Cl.
*A61L 2/28* (2006.01)
*A61L 2/07* (2006.01)
(52) U.S. Cl.
CPC ................. *A61L 2/28* (2013.01); *A61L 2/07* (2013.01); *A61L 2202/122* (2013.01);
(Continued)
(58) Field of Classification Search
CPC ... A61L 2/07; A61L 2202/14; A61L 2202/122
See application file for complete search history.

(56) References Cited

U.S. PATENT DOCUMENTS 5,422,276 A * 6/1995 Colvin ...................... A61L 2/28
422/26
7,701,334 B1 * 4/2010 Perkins .................. G16H 40/67
340/572.1
(Continued)

FOREIGN PATENT DOCUMENTS

DE    202011050118 U1    6/2011
DE    102015109415 A1    12/2016
(Continued)

OTHER PUBLICATIONS

Search Report received in German Application No. 10 2018 125 180.7 dated Jun. 6, 2019, with translation, 9 pages.
(Continued)

*Primary Examiner* — Jennifer Wecker
*Assistant Examiner* — Brady C Pilsbury
(74) *Attorney, Agent, or Firm* — Christopher A. Rothe; CM Law

(57) ABSTRACT

A sterilization packaging includes an interior space for receiving medical packaged goods and a sensor unit adapted to measure a first parameter in the interior space. The packaging has a data transmission unit for receiving and transmitting parameter values measured by the sensor unit. The packaging and data transmission unit are matched to one another to allow transmission of parameter values received by the data transmission unit into an outer space around the packaging. A sterilization method includes: introducing packaged goods into packaging and closing the packaging; introducing the closed packaging into a receiving chamber of a sterilizer; starting a sterilization process flow in the sterilizer; detecting parameter values in the packaging and transmitting the parameter values to a control unit of the sterilizer; and controlling the sterilization process flow as a function of the parameter values.

14 Claims, 4 Drawing Sheets

(52) U.S. Cl.
CPC ..... *A61L 2202/14* (2013.01); *A61L 2202/181* (2013.01); *A61L 2202/182* (2013.01); *A61L 2202/23* (2013.01); *A61L 2202/24* (2013.01)

(56) References Cited

U.S. PATENT DOCUMENTS

| | | | |
|---|---|---|---|
| 2005/0265889 A1* | 12/2005 | Wu | A61L 2/208 422/62 |
| 2006/0145840 A1* | 7/2006 | Klun | G01D 9/005 340/539.22 |
| 2010/0175393 A1 | 7/2010 | Burke et al. | |
| 2015/0190541 A1* | 7/2015 | Kitamura | A61L 2/28 422/26 |
| 2015/0374868 A1* | 12/2015 | Bruce | A61L 2/26 422/119 |
| 2017/0000919 A1* | 1/2017 | Childers | G01L 9/0072 |
| 2017/0224859 A1 | 8/2017 | Broninx et al. | |
| 2017/0348452 A1* | 12/2017 | Kuzelka | A61B 90/98 |
| 2018/0153639 A1 | 6/2018 | Wehrle et al. | |
| 2019/0290383 A1* | 9/2019 | Yaginuma | A61B 90/06 |
| 2021/0108969 A1* | 4/2021 | Fedegari | A61L 2/06 |
| 2021/0128761 A1* | 5/2021 | Schoville | G05D 23/1917 |

FOREIGN PATENT DOCUMENTS

| | | | |
|---|---|---|---|
| JP | 4750333 B2 * | 8/2011 | A61L 2/24 |
| WO | 2010083156 A1 | 7/2010 | |
| WO | 2010134826 A1 | 11/2010 | |
| WO | 2016188959 A1 | 12/2016 | |

OTHER PUBLICATIONS

International Search Report received in Application No. PCT/EP2019/077511 dated Jun. 23, 2020, with translation, 10 pages.

Written Opinion received in Application No. PCT/EP2019/077511 dated Jun. 23, 2020, with translation, 25 pages.

Office Acton received in Chinese Application No. 201980059876.4 dated Aug. 26, 2022, with translation, 25 pages.

* cited by examiner

STERILIZATION PACKAGING FOR STERILE PRODUCTS, HAVING A SENSOR DEVICE, AND STERILIZATION METHOD WITH ACTIVE STERILIZATION PROCESS ADAPTATION

CROSS-REFERENCE TO RELATED APPLICATION(S)

This application is the United States national phase entry of International Application No. PCT/EP2019/077511, filed Oct. 10, 2019, and claims the benefit of priority of German Application No. 10 2018 125 180.7, filed Oct. 11, 2018. The contents of International Application No. PCT/EP2019/077511 and German Application No. 10 2018 125 180.7 are incorporated by reference herein in their entireties.

FIELD

The present invention relates to a sterilization package for holding sterile goods, which has a sensor device or sensor unit for sterilization parameters. The invention relates in particular to a sterilization package for medical sterile items, for example surgical instruments or implants, and relates both to dimensionally stable sterilization packages, for example closable sterile containers with or without insertable baskets, and to soft sterilization packages, for example sterilization pouches or sterilization wraps, and individual (single) packages for surgical instruments or implants.

BACKGROUND

Medical articles must be sterilized before use. In the case of reusable articles, such as surgical instruments, this is usually ensured in hospital operations by placing the articles to be sterilized in a sterile container after use and cleaning, or by putting/wrapping them in a sterilization textile or film and then sterilizing them together with the sterile container or textile/film in a sterilizer (autoclave). Single-use items, such as implants, can also be sterilized in this way before use. Bacteria and viruses are deactivated in the receiving chamber of the sterilizer (sterilizer chamber) usually at a high temperature and, if necessary, overpressure and for a specific period of time. The specific target values for temperature, overpressure and duration depend on the sterility requirements and are determined for daily operation in the scope of a validation.

Following sterilization, a drying step is performed. Condensate, which is produced during sterilization, is dried in this step, since this is regarded as a potential site of risk for bacterial growth. The duration and temperature of the drying step are also determined as part of this validation.

A complete sterilization process sequence thus includes both a sterilization step and a drying step, which have to be validated for daily clinic operation. After successful validation, the sterilization process sequences then have the character of a standard for clinic operation, which is provided for specific items, item groups or specific container or sterilization packaging types to be sterilized. Typically, two or three different validated sterilization process sequences can be selected for the operation of the sterilizer. For example, a sterilization process sequence has a specific temperature and pressure profile, i.e., a specific temporal progression of temperature and pressure over the duration of the sterilization process sequence. The profiles of the different sterilization process sequences can differ in the process parameters temperature, pressure and time duration and can be selected depending on the sterilized items or sterilization packaging type. Once a sterilization process sequence has been validated, the target values of individual parameters and/or the intended profile of this sterilization process sequence may no longer be changed in daily clinic operation or, if a process parameter is changed, the modified sterilization process sequence has to be validated again.

When validating such a sterilization process sequence, a temperature sensor and a pressure sensor are first inserted into the interior of a sterilization package (container or wrap), which is packed with sterile items as an example. The temperature sensor and the pressure sensor are usually installed in a battery-powered recording module and, when switched on, record the measured temperature and the measured pressure on a storage medium in the recording module.

Before the validation sequence is started, the sterilization packages for which validation is to be performed are then placed in the sterilizer chamber together with the battery-powered recording module. Sensors for temperature and pressure are installed in the sterilizer's reception chamber as standard, and their values are continuously measured and recorded during sterilization operation. The recorded values can then be evaluated after the sterilization process sequence has been carried out.

The sequence of a sterilization process is rigidly programmed. For example, after a start-up time span, within which the target values for temperature and/or pressure are to be realized, a dwell time span is started, within which the values that have then been reached for temperature and/or pressure are maintained and within which the required sterilization and drying performance is expected in the sterilization packages.

As soon as the sterilization packages to be validated are in the sterilizer chamber, the sterilization process sequence to be validated can be started. During the sterilization process sequence to be validated, the temperature and pressure values are then measured and recorded via the sensors for temperature and pressure inside the sterilizer chamber, which are provided as standard.

After completion of the sterilization process sequence to be validated, the sterilization packages to be validated are removed from the sterilizer chamber, opened and the residual moisture in the sterilization package is determined and the recording module is removed. The recorded temperature and pressure measurement values from inside the sterilization package are then read out from the storage medium of the recording module. Now it is checked whether the required values for temperature and pressure were present inside the sterilization package over the provided period of time or whether the recorded time course of temperature and pressure corresponds to the provided profile.

If the check is positive, i.e. the measured residual moisture was within the target range and the required temperature and pressure were present inside the sterilization package for the required period of time, the measured temperature and pressure values from the sterilizer chamber and the period of time during which the temperature and pressure values were present in the sterilizer chamber or the measured temperature and pressure profile in the sterilizer chamber are defined as validated reference values and the sterilization process sequence performed is considered validated.

When the now validated sterilization process sequence for sterilizing medical articles is carried out, the measurement inside the sterilization package is omitted, so that the temperature and pressure are measured exclusively via the sensors of the sterilizer chamber, i.e. outside the sterilization package, during the execution of the sterilization process sequence. If the reference pressure and the reference temperature are realized in the sterilizer chamber for the duration of the reference time period, it is assumed that the required sterilization conditions have also been achieved inside the sterilization package.

In other words, for sterilization process sequences, after validation has been completed, measurements are only taken inside the sterilizer chamber and outside the sterilization package, and the sterilization success is inferred on the basis of the validation result. This is therefore an indirect sterilization control. The documentation of the sterilization process sequence performed for the treated sterilization packages is also only based on the values measured in the sterilizer chamber and comparison with the reference values of the validation.

However, this has the disadvantage that the validation results are no longer reliable as soon as the conditions under which the sterilization process sequence is carried out differ from the conditions under which the validation was carried out. Specifically, it often happens in everyday clinical practice that the sterilization packages are loaded with other medical articles, with a different number of pieces and/or a different packing arrangement. As a result, the predetermined target values of the sterilization parameters (temperature and pressure over the intended time span) may either not be reached at all inside the sterilization package, or the predetermined target values of the sterilization parameters may be reached much earlier inside the sterilization package than specified by the standard process, even though the temperature and pressure values recorded by the sensors of the sterilizer chamber correspond to the reference values of the validation. Similarly, it may happen that the intended degree of drying is not fully reached at the end of the reference time span for the drying step or that it is already reached well before the end of this reference time span.

Consequently, although validation of the containers is usually already carried out with maximum loading, in the cases mentioned first, in exceptional cases, there may be a risk to the patient if the loaded container (thus the medical articles contained therein) may not be sterile (at any point in the sterile container), and in the cases mentioned second, there is inefficient process management, since the sterilization process sequence takes an unnecessarily long time and an unnecessarily large amount of energy.

SUMMARY

It is thus an object of the present invention to overcome or at least reduce the disadvantages of the known sterilization process sequences described above. In particular, a sterilization package and a sterilization method are to be provided which enable both an efficient sterilization process sequence and ensure that the intended sterility and drying conditions are met.

In order to solve this object, the invention is based on the general idea of no longer controlling the sterilization process sequence (only) on the basis of the rigidly programmed sterilization process sequence and thus only indirectly conclude success of the sterilization via the values of the sterilization parameters temperature and pressure measured in the sterilizer chamber, i.e. in the exterior space around the sterilization package, but to carry out the sterilization process sequence also or exclusively via values of the sterilization parameters temperature and/or pressure and in particular relative (air) humidity measured in the interior space of the sterilization package and thus to carry out a direct control of the sterilization success.

In other words, according to the invention, measured values are to be used for controlling the sterilization process sequence and for sterilization control, which are measured where the packaged goods to be sterilized are located, namely in the interior space of the sterilization package. Control of the sterilization process sequence on the basis of the values measured in the interior space of the sterilization package requires data transmission of these measured values in real time to the control unit of the sterilizer. In the sense of the invention, a sterilization package is thus to be provided with which it is possible to determine measured values for the sterilization parameters temperature and/or pressure and/or humidity in the interior space of the sterilization package and to transmit the determined measured values in real time to the exterior space around the sterilization package to a data receiving unit of the sterilizer, which can use the received measured values or measured data from the interior space of the sterilization package by means of a control unit for controlling the sterilization process sequence.

Specifically, a sterilization package for medical packaged goods is proposed with an interior space which is provided and adapted to house the medical packaged goods, for example medical articles such as surgical instruments or implants, and at least one sensor unit which is provided and adapted to measure parameter values relating to the current sterilization process of at least a first parameter from the sterilization parameters of temperature, pressure and relative humidity in the interior space. In other words, the at least one sensor unit measures the values of temperature and/or pressure and/or relative humidity in the interior space. Furthermore, the sterilization package is provided with at least one data transmission unit which is provided and adapted to receive and transmit parameter values measured by the at least one sensor unit, and the sterilization package and the at least one data transmission unit are adapted to each other in such a way that they enable transmission of the parameter values received from the data transmission unit by means of the data transmission unit into an exterior space around the sterilization package.

In this case, the at least one sensor unit is in particular a temperature sensor unit and the sterilization package preferably has a further, second sensor unit which is a pressure sensor unit, so that at least the temperature and preferably also the pressure in the interior space of the sterilization package can be measured. This is advantageous since for common sterilization requirements, at least a high temperature, possibly in combination with high pressure (overpressure), has to be present and it can be checked by (a) corresponding sensor(s) whether the conditions in the interior space of the sterilization package meet the sterilization requirements.

Further preferably, the sterilization package has a further, third sensor unit that can determine the relative (air) humidity in the interior space of the sterilization package. In particular, the third sensor unit is a capacitive humidity sensor. It is advantageous to also determine the (relative) humidity in the interior space of the sterilization package, since common sterilization processes are carried out under the action of steam (for example, during autoclaving) and, in the drying step following the sterilization step, a humidity sensor can be used to determine whether the intended drying or the degree of drying to be achieved has been achieved.

In the case of several sensor units, data transmission to the exterior space around the sterilization package can be performed collectively via a single data transmission unit. In this case, this single data transmission unit receives the measured parameter values of all the sensor units provided and transmits them to the exterior space around the sterilization package. Alternatively, one data transmission unit per sensor unit can be provided, which only receives the parameter values determined by the assigned sensor unit and transmits them to the exterior space around the sterilization package. A common data transmission unit can also be provided for part of the plurality of sensor units, for example, a common data transmission unit for the temperature sensor and pressure sensor that receives the measured temperature and pressure values and transmits them to the exterior space, and another data transmission unit for the humidity sensor that receives the measured humidity values and transmits them to the exterior space. In this way, data transmission units can be used efficiently and according to the situation, while at the same time it is possible to retrofit individual sensor units and/or data transmission units.

The sterilization package can be a reusable, rigid package, for example a common sterile container with a flap or lid, or a (disposable) soft package. Current examples of soft packaging are sterilization pouches and sterilization wipes made of textile (special nonwoven) or foil, in which the sterilization material is inserted or wrapped (so-called "sterilization wrap").

Preferably, the parameter values received by the data transmission unit are transmitted (by means of the data transmission unit) via electromagnetic waves, for example WLAN, radio, or Bluetooth. This is advantageous because, particularly in the case of sterile requirements and the associated necessary recontamination barriers, a cable solution leads to high costs in the manufacture and regular inspection of the sterilization packages, since all cable passages in the sterilization package have to be verifiably sealed. In the case of wireless data transmission via electromagnetic waves, however, technical hurdles can arise in particular with sterile containers, which are usually made of a metal or a metal alloy, since metallic material has a shielding effect. In such a case, the coordination of the sterilization package, in particular the sterile container, and the data transmission unit plays a special role. For example, the wall thickness and/or the material of the sterile container can be adapted to the transmission power of the data transmission unit to allow the electromagnetic waves to pass through the container material. Alternatively or additionally, the data transmission unit can be selected or designed in such a way that its transmission power allows the electromagnetic waves to pass through the existing or provided container material. Thus, coordination of the data transmission unit and the sterile packaging unit with each other can be accomplished for existing containers in which the sensors and data transmission unit are to be retrofitted, as well as for new containers created specifically for this purpose. The same considerations apply to soft packaging in the form of metallic foils or metallic fabric.

Nevertheless, transmission of the parameter values received by the data transmission unit via a cable represents an alternative preferred solution, which is preferable in particular in cases of thick-walled or otherwise strongly shielding sterilization packages, in particular containers, or radiation-sensitive sterilization items or other radiation-sensitive components in the environment around the sterilization package. In these cases, the sterilization package can be equipped with specially sealed cable passages that meet the sterilization requirements. "Specially sealed and meeting the sterilization requirements" means in particular a seal which is both adapted to the high temperature, overpressure and/or humidity present during sterilization and which is suitable or adapted as a recontamination barrier. For example, in containers, the cable(s) of the sensors can be placed between the seal and the tray. A cable solution is also conceivable in which, for example, the sensors are installed in the lid and the cables are connected from the lid to the sterilizer.

Furthermore, it is preferred that the at least one data transmission unit is provided and adapted to transmit the received parameter values only when a predefined limit value is reached for a first parameter of the sterilization parameters temperature, pressure or humidity.

Further preferably, in a case in which the sterilization package is provided with at least one further, second sensor device, which is provided and adapted to detect parameter values (relating to the current sterilization process) of a second parameter from the aforementioned sterilization parameters in the interior space, and the at least one data transmission unit is provided and adapted for this purpose to receive and transmit the parameter values measured by the second sensor unit, the data transmission unit can be provided and adapted to transmit the received parameter values of the first and second parameters only when the predefined limit value for the first parameter and a predefined limit value for the second parameter are reached.

Accordingly, moreover, preferably in a case in which the sterilization package is provided with at least one further, third sensor device which is provided and adapted to detect parameter values (relating to the current sterilization process) of a third parameter from the aforementioned sterilization parameters in the interior space, and the at least one data transmission unit is provided and adapted for this purpose to receive and transmit the parameter values measured by the third sensor unit, the data transmission unit can be provided and adapted to transmit the received parameter values of the first, second and third parameters only when the predefined limit value for the first parameter, the predefined limit value for the second parameter or a predefined limit value for the third parameter is reached.

In this way, the period of time during which the data transmission unit transmits measured values to the exterior space can be limited to the period of time that is essential for controlling the sterilization process sequence and checking the success of sterilization. Consequently, a sterilization-proof battery or another sterilization-proof energy source to which the data transmission unit is connected can be conserved and energy consumption can be reduced.

Preferably, the at least one sensor unit and/or the at least one data transmission unit is permanently installed with the sterilization package. This is relevant in particular for reusable sterile containers. The fixed installation ensures that the provided data transmission unit is also coordinated with the provided sterilization package and vice versa. An unfavorable combination of data transmission unit and sterilization package made by the user, which are not coordinated with each other and do not allow transmission of the parameter values received by the data transmission unit to the exterior space around the sterilization package, can thus already be prevented by the manufacturer.

In particular, it is preferred that the sterilization package is a sterile container comprising a container tray and an associated container lid, and that the at least one sensor unit and/or the at least one data transmission unit, which is fixedly installed with the sterilization package, is fixedly installed with the container tray or the container lid, preferably the container lid. Associated container lid means a lid for the container tray that is provided and adapted to tightly seal the container tray in accordance with sterilization requirements. Container lids often fit different container trays of different sizes/volumes. The selection of the container tray in operation is based, for example, on the size/volume of the packaged goods, and the container tray is then closed with a lid suitable for each of the different container trays. If the at least one sensor unit and/or the at least one data transmission unit is arranged fixedly in the lid, this has the advantage that the costs of manufacture or retrofitting can be kept low, since not necessarily as many lids as container trays have to be provided in hospital operation. Alternatively, it is preferred that the at least one sensor unit and/or the at least one data transmission unit can also be arranged on the container tray or on a basket into which the packaged goods are placed and which is placed in the container tray. In terms of costs, it is advantageous to arrange the at least one sensor unit and/or the at least one data transmission unit on the component (lid, tray or basket) that has the lowest wear-related replacement frequency.

Alternatively, it is preferred that the at least one sensor unit and/or the at least one data transmission unit is assembled to form a sterilization-proof, separate, encapsulated module, and that the module is provided and adapted to be freely placeable in the interior space. The module may also be attached to a sieve basket of the sterilization package. A separate module means a module that is not (fixedly) connected to the sterilization package and is available or freely movable independently of the sterilization package. Such a module can be added to the packaged item in the interior space of the sterilization package prior to the sterilization process sequence and then remains in the sterilization package until the sterilized item is used. This has the advantage that the (wear-related) exchange of parts of the sterilization packages (lid, tray, basket) can be carried out independently of the at least one sensor unit and/or the at least one data transmission unit. Disposable sterilization packages such as sterilization wipes or films (sterilization wraps) can easily be accompanied by a separate module. The module further comprises a sterilization-proof, rechargeable battery or a sterilization-proof energy source, in particular designed such that the stored energy is sufficient for at least one sterilization process sequence.

Preferably, the at least one data transmission unit is further provided and adapted to receive signals from the exterior space, and the sterilization package and the at least one data transmission unit are adapted to each other in such a way that reception of the signals from the exterior space is possible. In this way, the data transmission unit can be switched off and energy can be saved by a signal received from the exterior space, for example when a target state is reached in the interior space of the sterilization package.

Furthermore, a sterilization system is provided according to the invention. The sterilization system according to the invention is provided with a sterilizer and at least one sterilization package, wherein the sterilizer comprises a reception chamber for receiving the at least one sterilization package, at least one data receiving unit arranged in the exterior space around the at least one sterilization package, and a control unit, and the control unit is provided and adapted to be in information exchange contact with the data receiving unit and to control a sterilization process sequence in the reception chamber. In this respect, the at least one sterilization package is one of the sterilization packages described above, the at least one data receiving unit is provided and adapted to receive the parameter values transmitted by the at least one data transmission unit of the sterilization package and to forward them to the control unit, and the control unit is provided and adapted to control the sterilization process sequence in dependence on the parameter values received by the data receiving unit.

In this way, it is possible for the sterilizer to carry out and adapt the sterilization process sequence taking place in the receiving chamber depending on the real conditions on the sterilized items, namely in the interior space of the sterilization package. The sterilization process sequence can therefore be adapted or oriented to the real conditions in real time in such a way that a defined sterilization and/or drying target is reliably achieved and the time required to achieve it or the total sterilization process time is kept as short as possible.

In the context of the invention, a sterilization method for medical packaged goods is further proposed comprising the following steps: i) placing the packaged goods in an interior space of a sterilization package and then closing the sterilization package; thereafter ii) placing the closed sterilization package in a reception chamber of a sterilizer; thereafter iii) starting a (pre-programmed) sterilization process sequence in the sterilizer, wherein the start and execution of the sterilization process sequence are performed by a control unit in the sterilizer. Thereby, the sterilization method further comprises the steps of: vi) detecting parameter values in the interior space of the sterilization package and transmitting these detected parameter values (in real time) to the control unit of the sterilizer; and vii) controlling the sterilization process sequence depending on the parameter values detected in the interior space.

In other words, the method according to the invention provides for starting a sterilization process sequence manually entered by the user or selected from the program library of the sterilizer after a sealed sterilization package, in the interior space of which there are packaged items to be sterilized, has been introduced into the reception chamber of the sterilizer, and to measure at least one parameter, preferably two parameters and further preferably three parameters from the sterilization parameters temperature, pressure and/or humidity in the interior space of the sterilization package and to control the sterilization process sequence in dependence on the measured parameter values. The control of the sterilization process sequence can optionally be supported by parameter values determined in the reception chamber of the sterilizer.

The transmission of the measured parameter values from the interior space of the sterilization package to the control unit of the sterilizer has the advantage that the sterilization performance is detected directly on the sterilization items and can be actively adapted to the sterilization items accordingly. The sterilization process sequence can thus be optimized, since active control means that detection takes place in real time when the target state is reached inside the sterilization chamber. Premature termination of the sterilization process sequence or a sterilization process sequence that goes beyond reaching the target state is prevented. This ensures that the sterilization target is always reached and that the sterilization process sequence nevertheless remains efficient. In addition, if there are several sterilization packages in the reception chamber of the sterilizer, separate, individual proof of sterilization is provided for each of these sterilization packages.

Preferably, the sterilization method according to the invention is carried out with the aforementioned sterilization package.

BRIEF DESCRIPTION OF THE DRAWING FIGURES

The invention is described hereinafter by means of preferred exemplary embodiments with reference to the accompanying drawings. They show:

DETAILED DESCRIPTION

The figures are merely schematic in nature and serve solely the purpose of understanding the invention. The same elements are provided with the same reference signs. The features of the individual exemplary embodiments can be interchanged.

Figure 1:
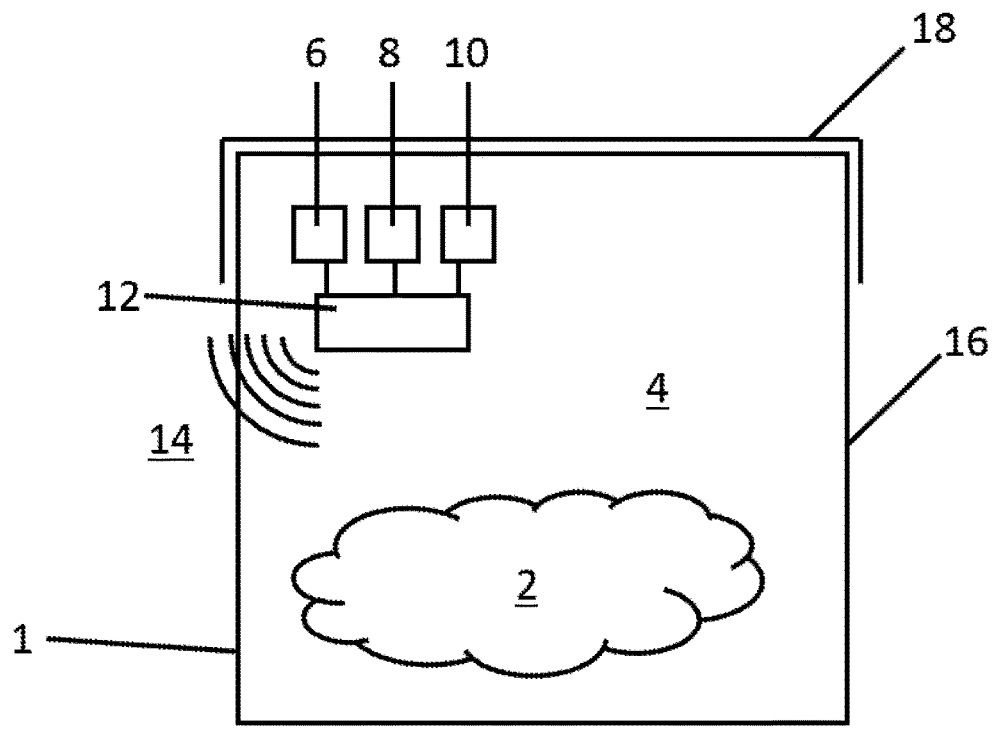
FIG. 1 shows a schematic representation of a sterilization package according to a first exemplary embodiment of the invention.

FIG. 1 shows a schematic representation of a sterilization package 1 for a medical packaged item 2 according to a first exemplary embodiment of the invention. The sterilization package 1 has an interior space 4 into which the medical packaged item 2 is inserted. A temperature sensor unit 6 that measures the temperature in the interior space 4, a pressure sensor unit 8 that measures the pressure in the interior space 4, and a humidity sensor unit 10 that measures the relative humidity in the interior space 4 are arranged on the sterilization package 1. Furthermore, a data transmission unit 12 is arranged on the sterilization package 1. The sensor units 6, 8, 10 are connected to the data transmission unit 12 via cables and transmit the measured parameter values to the data transmission unit 12. The data transmission unit 12 transmits the received parameter values to the exterior space 14 around the sterilization package 1. Electromagnetic waves are used for transmission, for example via WLAN, radio or Bluetooth. Alternatively, any other data transmission standard is conceivable. In this exemplary embodiment, the sterilization package 1 is a sterile container comprising a tray 16 and a lid 18. The sensor units 6, 8, 10 are fixedly installed in the sterile container 1.

Figure 2:
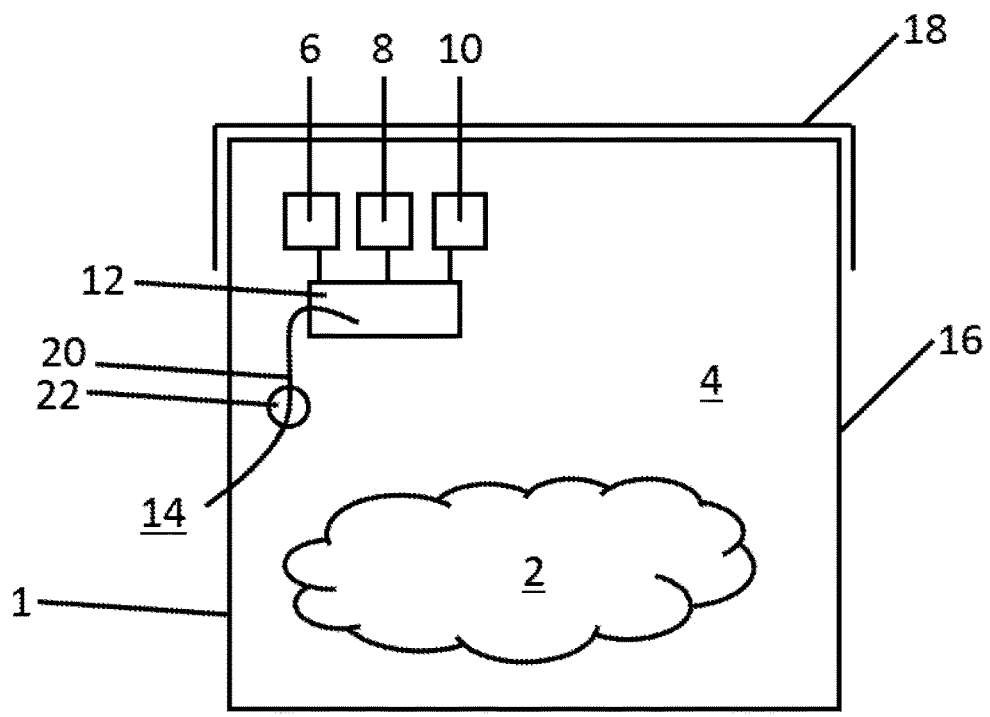
FIG. 2 shows a schematic representation of a sterilization package according to a second exemplary embodiment of the invention.

FIG. 2 shows a schematic representation of a sterilization package 1 for a medical packaged item 2 according to a second exemplary embodiment of the invention. The sterilization package 1 according to the second exemplary embodiment corresponds essentially to the first exemplary embodiment shown in FIG. 1, with the difference that the data transmission unit 12 does not transmit the received parameter values to the exterior space 14 via electromagnetic waves, but instead has a cable 20 which, starting from the data transmission unit 12, extends into the exterior space 14 through an opening 22 in the container wall. In this regard, the cable 20 can be passed through the wall of the container tray or through the container lid. Likewise, a passage of the cable 20 between the lid and the tray is conceivable. The opening 22 is sealed in accordance with the requirements of a recontamination barrier suitable for sterility. The cable 20 can be used to connect the data transmission unit 12 to an external data receiving unit (not shown).

Figure 3:
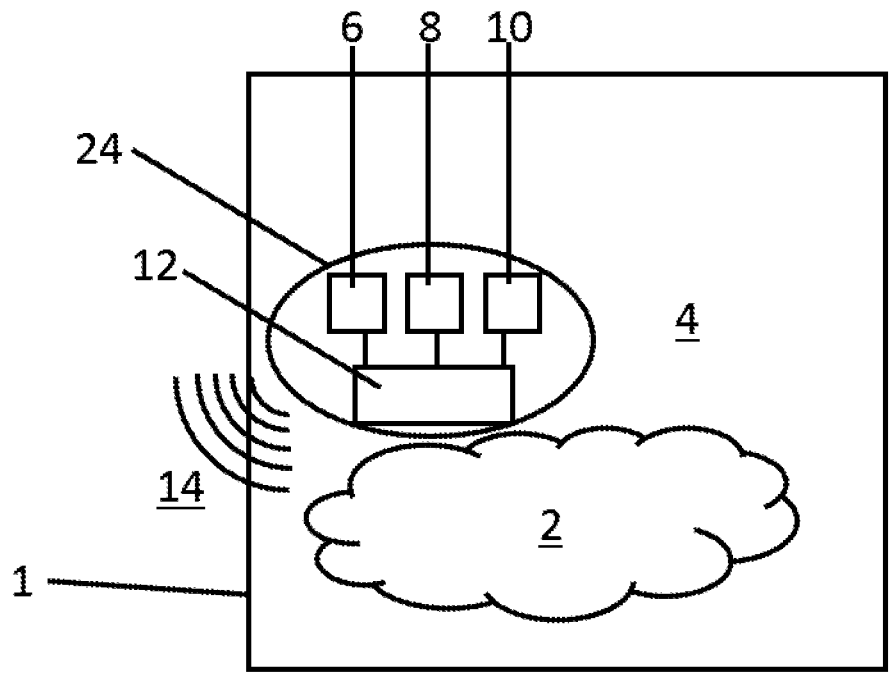
FIG. 3 shows a schematic representation of a sterilization package according to a third exemplary embodiment of the invention.

FIG. 3 shows a schematic representation of a sterilization package 1 for a medical packaged item 2 according to a third exemplary embodiment of the invention. The sterilization package 1 according to the third exemplary embodiment corresponds essentially to the first exemplary embodiment shown in FIG. 1, with the difference that the sensor units 6, 8, 10 and the data transmission unit 12 are not fixedly connected to the sterilization package 1, but are installed in a separate, encapsulated module 24. The separate module 24 is spatially independent of the sterilization package 1 and can be freely placed. As in the first exemplary embodiment, the data transmission unit 12 transmits the received parameter values via electromagnetic waves into the exterior space 14. In this third exemplary embodiment, the sterilization package 1 can also be a sterile container or a soft package, for example in the form of a sterilization wrap.

Figure 4:
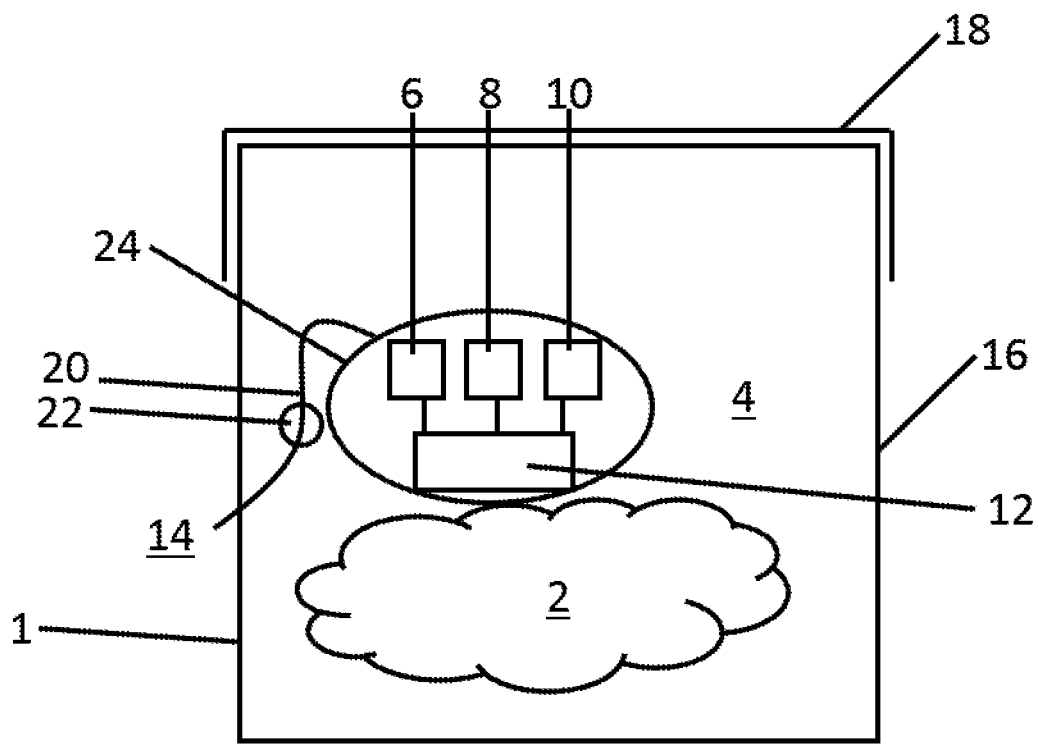
FIG. 4 shows a schematic representation of a sterilization package according to a fourth exemplary embodiment of the invention.

FIG. 4 shows a schematic representation of a sterilization package 1 for a medical packaged item 2 according to a fourth exemplary embodiment of the invention. The sterilization package 1 according to the fourth exemplary embodiment corresponds essentially to the third exemplary embodiment shown in FIG. 3, with the difference that the separate module 24 does not transmit the received parameter values to the exterior space 14 via electromagnetic waves, but instead has a cable 20 which, starting from the data transmission unit 12 installed in the module 24, extends into the exterior space 14 through an opening 22 in the sterilization package wall. In this exemplary embodiment, the sterilization package 1 is a sterile container and the opening 22 is sealed in accordance with the requirements of a recontamination barrier suitable for sterility. The data transmission unit 12 can be connected to an external data receiving unit (not shown) via the cable 20.

Figure 5:
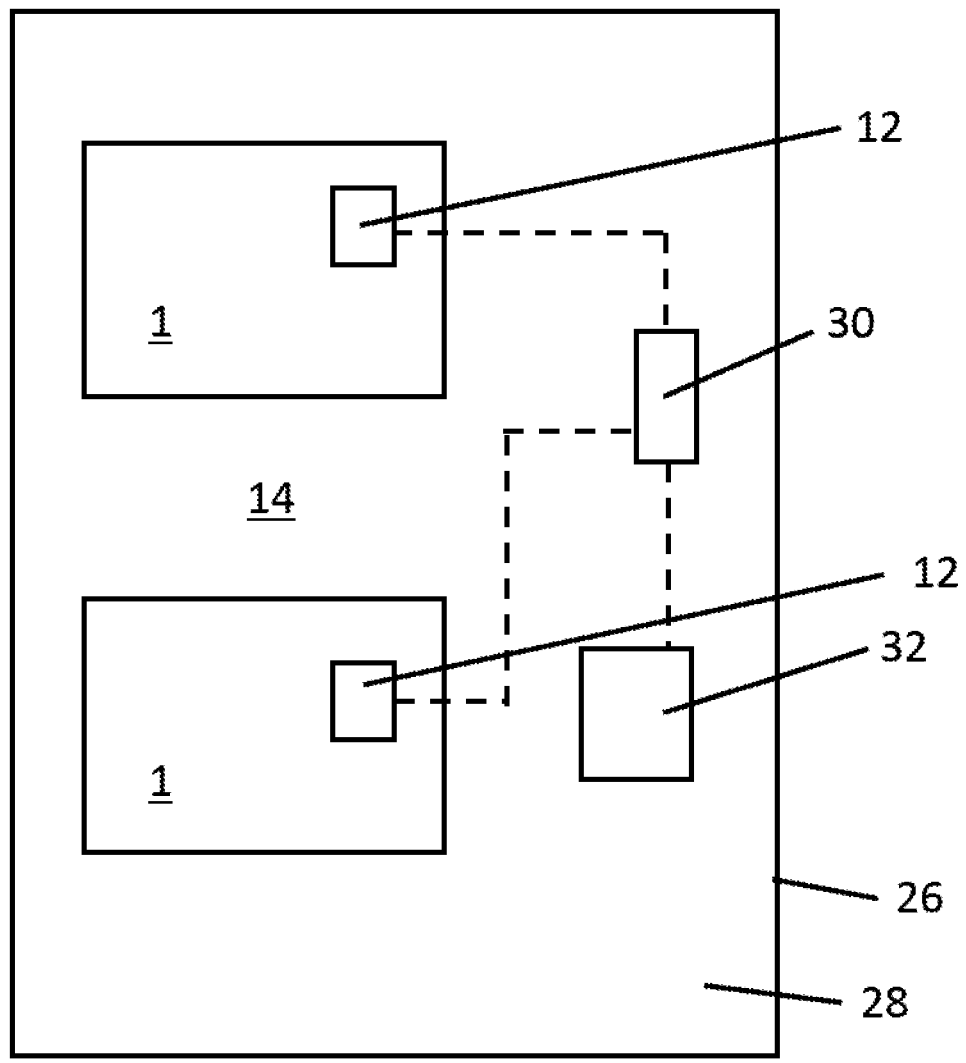
FIG. 5 shows a schematic representation of a sterilization system according to the invention.

FIG. 5 shows a schematic representation of a sterilization system according to the invention. The sterilization system has a sterilizer 26 with a reception chamber 28 into which one or more sterilization packages 1 can be placed, a data receiving unit 30, and a control unit 32. During sterilization, measured values are transmitted from the data transmission unit 12 arranged in the interior space of the sterilization packages 1 to the data receiving unit 30 arranged in the exterior space 14 around the sterilization packages 1. The data receiving unit 30 transmits the measured values to the control unit 32, which controls the sterilization process sequence depending on the measured values from the interior space of the sterilization packages 1. The sterilization packages 1 may be one or more (different ones) of the sterilization packages 1 described above, i.e. containers and/or soft packages with data transmission via electromagnetic waves and/or cables and fixedly installed and/or modularly incorporated sensor units.

Figure 6:
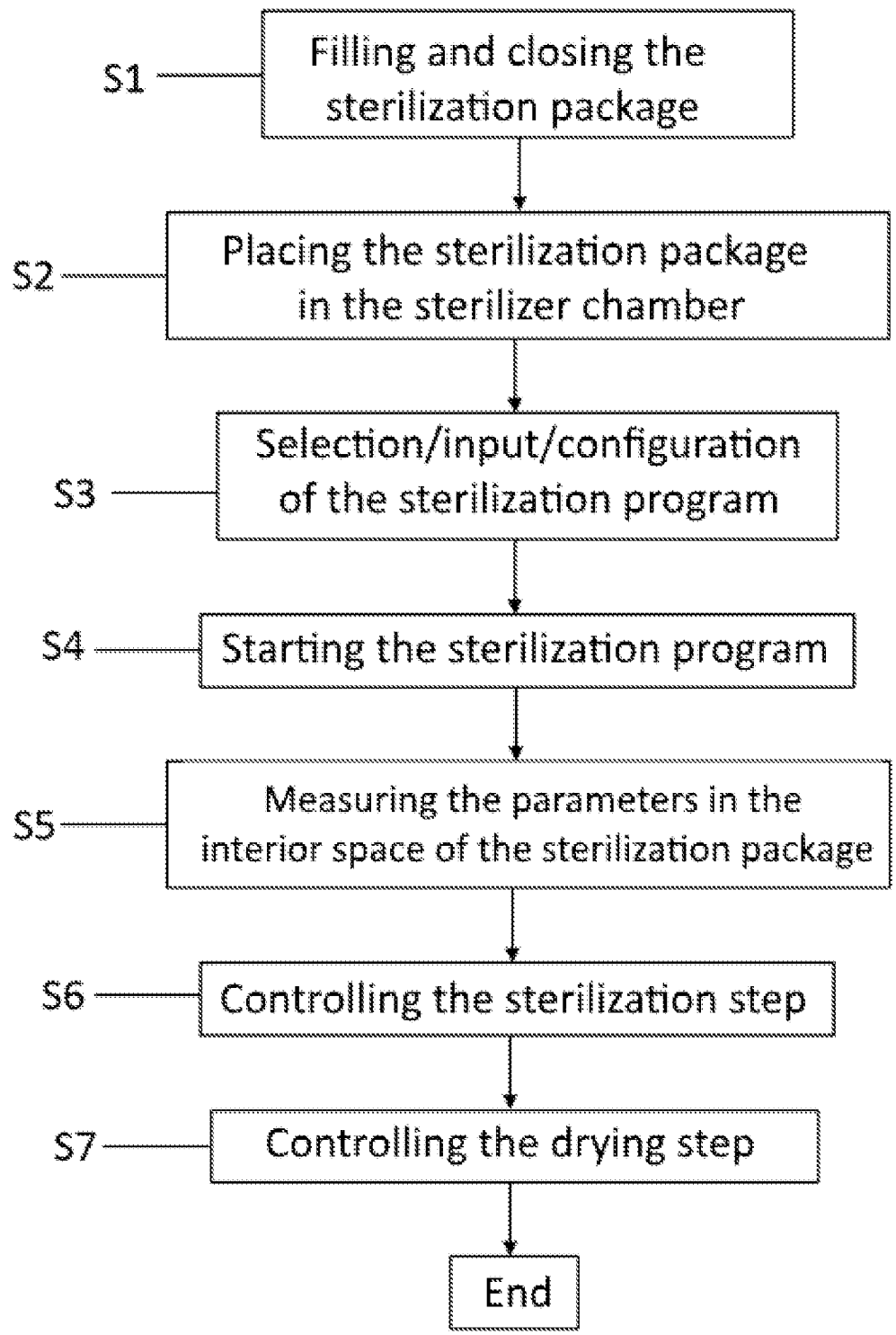
FIG. 6 shows a schematic representation of a sterilization method according to the invention.

FIG. 6 shows a schematic diagram of a sterilization method according to the invention. In step S1, a sterilization package is first filled with sterilization items and sealed. The sterilization package either has a separate module with a pressure sensor unit, a temperature sensor unit, a humidity sensor unit and a data transmission unit, or the sensor units and the data transmission unit are fixedly installed in the sterilization package. The sealed sterilization package is then placed in the reception chamber of a sterilizer in step S2.

In step S3, the user either manually enters a sterilization process sequence (sterilization program) into the sterilizer control via a user interface or the user selects and optionally adapts a preprogrammed sterilization program. The selection and adaptation can be made, for example, depending on the type of sterilization packaging present or the load with sterilization items. Target temperatures, target pressures, values for the relative humidity to be achieved and the duration over which one or more target values are to be maintained can be adjusted.

A complete sterilization program has a sterilization step and a drying step. An exemplary sterilization step has a target temperature value of 134° C. at a target pressure value of 3.1 bar and lasts (in total) 25 min to 35 min. The drying step can last from a few minutes to more than half an hour. During the sterilization step, the target temperature and pressure are maintained for a predetermined period/time span. Specifically, in order to inactivate bacteria and viruses, it is necessary that a temperature of at least 134° C. is reached in the entire interior of the container, i.e. also in crevices and between the loading, and is maintained for at least 3 min purely according to standards. However, due to the compensation time until all container areas have reached the required temperature, in practice the dwell time is usually extended to 5 min. Low-temperature sterilization methods, in which the normative minimum dwell time is 15 min at 121° C., are not very common. The DIN standard DIN EN 285:2015 is also relevant here.

It is also possible for the sterilization step to have several successive process sections with different target parameter values, each of which has to be present for a certain period of time. For example, prior to the actual sterilization, various vacuum cycles are run at 3.1 bar and 134° C. in order to evacuate contaminated air from the container. After each vacuum cycle, the vacuum is balanced by (sterile) water vapor.

The sterilization step is followed by the drying step, in which the water produced during the steam action in the sterilization package is evaporated and the sterilization items are thus dried. Drying parameters can be temperature and relative humidity, optionally pressure, or just temperature and a required time span in which a target temperature has to be present. The humidity sensor can be used to determine whether the desired degree of drying has been achieved. After configuration of the sterilization program, the sterilization program is started in step S4.

After the sterilization program has started, in step S5 the sterilization parameters temperature, pressure and relative humidity in the interior space of the sterilization package are now measured continuously or at specific intervals and are transmitted to the control unit of the sterilizer. For this purpose, the data transmission unit located in the interior space of the sterilization package sends the parameter values received from the sensor units to the control unit of the sterilizer in the exterior space around the sterilization package. While step S5 continues to be executed, step S6 is started. The two steps S5 and S6 then run in parallel until the end of step S6.

In step S6, the sterilizer control unit compares the measured values received in step S5 with the target parameters (target values) defined in step S3 from the configured sterilization program. Once the target parameters have been reached, the defined (dwell) time span starts to run. During this time span, the measurement of the parameters continues as in step S5 and the control unit compares the measured values with the target values. This serves as a check, since the defined target parameter values have to be present for the entire defined time period (dwell time). If one of the measured values falls below a tolerance range of the target value, the defined time span is reset to 0 and step S6 starts again from the beginning. If the defined target parameter values remain within the target range until the end of the defined time span, the sterilization target is considered to have been reached. In the case of a sterilization step that has several process sections, each with different target parameter values and associated (dwell) time periods, step S6 is run for each individual process section in turn, and once the process section target of the last process section has been reached, the sterilization target is considered to have been reached. Sterilization step S6 is then terminated and the sterilization program is then continued to step S7.

In step S7, the defined drying step is started. As in step S6, step S5 also continues in parallel with step S7. In step S7, the control unit compares the measured parameter values with the defined target parameter values of the drying step. The drying step is considered complete when the measured relative humidity reaches the defined target value. Alternatively, the drying step is considered complete if instead of a target value for the relative humidity only a required time span has been defined and the defined time span has been passed. If the drying step is completed, steps S7 and step S5 executed in parallel are terminated and the sterilization program is over.

The sterilization process sequence is thus monitored and adapted or controlled in real time and as a function of the sterilization parameters measured on the sterilization items, i.e. in the interior space of the sterilization package. Validation sequences and indirect process controls preceding the sterilization process sequences thus become obsolete and are replaced by the method according to the invention, which enables more efficient and safer process control. Optionally, parameters measured in the reception chamber can be used and documented to support process control.

By recording the real-time data, a check can be made for each individual sterilization package and the sterilization result or the ID of the sterilization package can be electronically linked to the patient file. The method according to the invention thus also offers the possibility of simplified and consistent electronic clinical documentation.

The invention claimed is:

1. A sterilization package for medical packaged items, the sterilization package comprising:
    an interior space which is provided and adapted to house the medical packaged items; and
    at least one sensor unit which is provided and adapted to measure parameter values relating to a current sterilization process of at least a first parameter from the sterilization parameters of temperature, pressure and relative humidity in the interior space,
    the sterilization package being provided with at least one data transmission unit which is provided and adapted to receive said parameter values measured by the at least one sensor unit and transmit said parameter values in real time only when a predefined limit value for the first parameter is reached, and
    the sterilization package and the at least one data transmission unit being adapted to each other in such a way that said parameter values received by the at least one data transmission unit are transmitted from the interior space and wirelessly through a metallic wall of the sterilization package to an exterior space around the sterilization package in real time only when the predefined limit value for the first parameter is reached,
    wherein the at least one data transmission unit is further provided and adapted to receive signals from the exterior space and wirelessly through the metallic wall of the sterilization package to the interior space, and the sterilization package and the at least one data transmission unit are adapted to each other in such a way that reception of the signals from the exterior space is possible, and the at least one data transmission unit is capable of being switched off by a signal of the signals received from the exterior space.

2. The sterilization package according to claim 1, wherein transmission of the parameter values received by the at least one data transmission unit is performed via electromagnetic waves.

3. The sterilization package according to claim 1, wherein the sterilization package is equipped with at least one further sensor unit which is provided and adapted to measure parameter values relating to the current sterilization process of a second parameter from the sterilization parameters temperature, pressure and relative humidity in the interior space, and the at least one data transmission unit is provided and adapted to receive and transmit the parameter values measured by the at least one further sensor unit, and the at least one data transmission unit is provided and adapted to transmit received parameter values only when the predefined limit value for the first parameter and a predefined limit value for the second parameter are reached.

4. The sterilization package according to claim 1, wherein the at least one sensor unit and/or the at least one data transmission unit are fixedly installed in the sterilization package.

5. The sterilization package according to claim 4, wherein the sterilization package is a sterile container comprising a container tray and an associated container lid, and the at least one sensor unit and/or the at least one data transmission unit, which is fixedly installed in the sterilization package, is fixedly installed in the associated container lid or the container tray.

6. The sterilization package according to claim 1, wherein the at least one sensor unit and the at least one data transmission unit are assembled into a separate, encapsulated module adapted to be freely placeable in the interior space.

7. The sterilization package according to claim 6, wherein an entirety of the at least one data transmission unit is assembled into the separate, encapsulated module, and the at least one data transmission unit is configured to transmit the parameter values to an exterior space of a sterilizer containing the sterilization package and the separate, encapsulated module.

8. The sterilization package according to claim 1, wherein the at least one data transmission unit can be switched off and energy can be saved by a signal of the signals received from the exterior space, when a target state is reached in the interior space of the sterilization package.

9. A sterilization system comprising a sterilizer and at least one sterilization package, wherein the sterilizer comprises a reception chamber for receiving the at least one sterilization package, at least one data receiving unit arranged in an exterior space around the at least one sterilization package, and a control unit provided and adapted to be in information exchange contact with the at least one data receiving unit and to control a sterilization process in the reception chamber, the at least one sterilization package comprising a sterilization package according to claim 1,
the at least one data receiving unit being provided and adapted to receive the parameter values transmitted by the at least one data transmission unit of the sterilization package and to forward them to the control unit, and
the control unit being provided and adapted to control the sterilization process in dependence on the parameter values received from the at least one data receiving unit.

10. The sterilization system according to claim 9, wherein the at least one sensor unit and the at least one data transmission unit are assembled into a separate, encapsulated module adapted to be freely placeable in the interior space.

11. A sterilization method for medical packaged items comprising the steps of:
i) placing the medical packaged items in an interior space of a sterilization package and closing the sterilization package;
ii) placing the sterilization package in a reception chamber of a sterilizer;
iii) starting a sterilization process sequence in the sterilizer by a control unit of the sterilizer;
iv) detecting parameter values of at least a first one of the sterilization parameters of temperature, pressure, and relative humidity in the interior space of the sterilization package and transmitting, by at least one data transmission unit in the sterilization package, said parameter values from the interior space and wirelessly through a metallic wall of the sterilization package to an exterior space around the sterilization package in real time only when a predefined limit value for said first one of the sterilization parameters is reached to the control unit of the sterilizer; and
v) controlling the sterilization process sequence as a function of the parameter values,
wherein the sterilization method further comprises steps of:
vi) receiving signals from the exterior space and wirelessly through the metallic wall of the sterilization package to the interior space; and
vii) switching off the at least one data transmission unit by a signal of the signals received from the exterior space.

12. The sterilization method according to claim 11, wherein the sterilization package comprises:
an interior space which is provided and adapted to house the medical packaged items; and
at least one sensor unit which is provided and adapted to measure parameter values relating to the sterilization process sequence of at least a first parameter from the sterilization parameters of temperature, pressure and relative humidity in the interior space,
the sterilization package being provided with at least one data transmission unit which is provided and adapted to receive the parameter values measured by the at least one sensor unit in real time and to transmit the parameter values received by the at least one data transmission unit into the exterior space around the sterilization package in real time only when the predefined limit value for the first parameter is reached.

13. The sterilization method according to claim 12, wherein the at least one sensor unit and the at least one data transmission unit are assembled into a separate, encapsulated module adapted to be freely placeable in the interior space.

14. The sterilization method according to claim 11, wherein the step vii) comprises switching off the at least one data transmission unit by a signal of the signals received from the exterior space, when a target state is reached in the interior space of the sterilization package.

\* \* \* \* \*